(12) United States Patent
Pinkos et al.

(10) Patent No.: US 8,383,866 B2
(45) Date of Patent: Feb. 26, 2013

(54) PROCESS FOR PREPARING DIOLS BY HYDROGENATING A CARBOXYLIC ACID-COMPRISING MIXTURE BY MEANS OF COBALT-COMPRISING CATALYSTS

(75) Inventors: Rolf Pinkos, Bad Duerkheim (DE); Axel Paul, Lampertheim (DE); Rolf-Hartmuth Fischer, Heidelberg (DE); Roman Dostalek, Neuleiningen (DE)

(73) Assignee: BASF SE, Ludwigshafen (DE)

( * ) Notice: Subject to any disclaimer, the term of this patent is extended or adjusted under 35 U.S.C. 154(b) by 192 days.

(21) Appl. No.: 12/953,004

(22) Filed: Nov. 23, 2010

(65) Prior Publication Data

US 2011/0124926 A1    May 26, 2011

(30) Foreign Application Priority Data

Nov. 26, 2009  (DE) .................. 10 2009 047 193

(51) Int. Cl.
*C07C 29/156* (2006.01)
(52) U.S. Cl. .................................................... 568/864
(58) Field of Classification Search .................. 568/864
See application file for complete search history.

(56) References Cited

U.S. PATENT DOCUMENTS

| | | | |
|---|---|---|---|
| 3,478,112 A | 11/1969 | Adam et al. | |
| 4,940,805 A | 7/1990 | Fischer et al. | |

FOREIGN PATENT DOCUMENTS

| | | |
|---|---|---|
| DE | 1 235 879 | 3/1967 |
| DE | 2 321 101 | 11/1974 |
| DE | 197 56 171 A1 | 7/1999 |
| EP | 0 304 696 A1 | 8/1988 |
| EP | 0 382 050 A1 | 1/1990 |
| WO | WO 2010/063659 A2 | 6/2010 |
| WO | WO 2010/115738 A1 | 10/2010 |

OTHER PUBLICATIONS

International Search Report issued Mar. 9, 2011 in Corresponding PCT/EP2010/067973 (with English translation of Category of Cited Documents).
U.S. Appl. No. 13/510,115, filed May 16, 2012, Tompers, et al.
U.S. Appl. No. 13/133,006, filed Jun. 6, 2011, Abillard, et al.
U.S. Appl. No. 13/257,496, filed Sep. 19, 2011, Pinkos, et al.
U.S. Appl. No. 13/226,049, filed Sep. 6, 2011, Abillard, et al.
U.S. Appl. No. 12/952,861, filed Nov. 23, 2010, Pinkos, et al.
U.S. Appl. No. 12/952,956, filed Nov. 23, 2010, Pinkos.

*Primary Examiner* — Sikarl Witherspoon
(74) *Attorney, Agent, or Firm* — Oblon, Spivak, McClelland, Maier & Neustadt, L.L.P.

(57) ABSTRACT

The present invention relates to a process for preparing diols by hydrogenating a mixture comprising carboxylic acid, carboxylic anhydrides and/or carboxylic esters/lactones by means of a cobalt-comprising catalyst, wherein alkali metal and/or alkaline earth metal ions are added to the hydrogenation feed, excluding alkali metal and/or alkaline earth metal ions of mineral acids.

9 Claims, No Drawings

PROCESS FOR PREPARING DIOLS BY HYDROGENATING A CARBOXYLIC ACID-COMPRISING MIXTURE BY MEANS OF COBALT-COMPRISING CATALYSTS

The present invention relates to a process for preparing diols by hydrogenating a mixture comprising carboxylic acid, carboxylic anhydrides and/or carboxylic esters/lactones by means of a cobalt-comprising catalyst, wherein alkali metal and/or alkaline earth metal ions are added to the hydrogenation feed, excluding alkali metal and/or alkaline earth metal ions of mineral acids.

U.S. Pat. No. 4,940,805, EP-A 304 696, EP-A 382 050, DE-B 12 35 879 and DE-A 23 21 101 describe catalysts comprising cobalt and optionally manganese for hydrogenation of carboxylic acids, carboxylic anhydrides or carboxylic esters/lactones to the corresponding diols. A disadvantage of these catalysts is that they are unstable in the presence of acids and water, in that they gradually lose the active components, such as Co and optionally Mn. This has an adverse effect on the catalyst service life. Moreover, there is dehydration and/or etherification of the diol which forms during the hydrogenation over the acidic catalyst sites, and hence a decrease in yield of the diol to be prepared. As a result of the formation of these by-products, the diol obtained has to be sent to further purification steps such as distillations, which again reduces the yield of the diol obtained.

DE-A 12 35 879 likewise describes the hydrogenation of carboxylic acids over catalysts comprising cobalt and manganese, wherein the activity and service life are improved by adding acids which can form polyacids, or the alkali metal, alkaline earth metal or earth metal salts thereof. The addition can be effected during the catalyst preparation or via the feed, as disclosed in Example 16 of DE-A 12 35 879. Example 16 of DE-A 12 35 879 describes performing the hydrogenation of a carboxylic acid mixture comprising, inter alia, adipic acid, glutaric acid, succinic acid, 6-hydroxycaproic acid, already hydrogenated carboxylic acid mixture and an undefined amount of crude monoalcohols, the water content of which has been adjusted to 7%, with 0.1% by weight of $Na_3PO_4$. A disadvantage of this process is that the addition of sodium phosphate, as an alkali metal salt of a mineral acid, to the hydrogenation feed does not bring about an increase in the activity and service life of the catalyst, and on the contrary leads to reduced yields of the desired end product with increased depletion of the active catalyst metals.

It is therefore an object of the present invention to provide a process for preparing diols, which enables the discharge of Co ions and any Mn ions from the cobalt-comprising catalyst used to be reduced, the initial catalyst activity thus to be maintained for as long as possible, and the catalyst service life to be prolonged, and also the further reaction of the desired diols to give by-products, especially to give hexanol and, if aqueous wash extracts from cyclohexane oxidation with air are used, cyclohexyl 1,6-hexanediol ether, to be reduced. These elimination and etherification reactions, which, as side reactions, are generally acid-catalyzed reactions, are usually associated with the elimination of water and cause a reduction in the yield of the diol to be prepared. It is thus also a further object of the process according to the invention to increase the yield of the desired diol, especially 1,6-hexanediol.

This object is achieved by a process for preparing diols by hydrogenating a mixture comprising carboxylic acid, carboxylic anhydrides and/or carboxylic esters/lactones by means of a cobalt-comprising catalyst, wherein alkali metal and/or alkaline earth metal ions are added to the hydrogenation feed, excluding alkali metal and/or alkaline earth metal ions of mineral acids.

In the process according to the invention, a mixture comprising carboxylic acid, carboxylic anhydride and/or carboxylic esters/lactones is hydrogenated by means of a cobalt-comprising catalyst. The carboxylic acid, carboxylic anhydride and/or lactones present in the mixture to be hydrogenated may be selected from the group of maleic anhydride, maleic acid, succinic anhydride, succinic acid, glutaric acid, citric acid, itaconic acid, adipic acid, hydroxycaproic acid, caprolactone, or are the aqueous extract which arises through oxygen oxidation of cyclohexane to cyclohexanol/cyclohexanone mixtures and subsequent extraction with water. The hydrogenation can be performed in substance, i.e., for example, in the melt, or in solvents, for example alcohols such as methanol, ethanol, etc., or inert solvents such as tetrahydrofuran, dioxane or diethyl ether, or in water. It is also possible for noncyclic esters to be present in the mixture to be hydrogenated, but not as the main component. Based on the acids or anhydrides or lactones, the content thereof in the feed is below 20 mol %. The ester content may rise during the hydrogenation.

When alkali metal and/or alkaline earth metal ions which are not salts of a mineral acid are added to the hydrogenation feed, it is possible firstly to reduce the Co discharge and if appropriate Mn discharge and hence to prolong the catalyst service life, and secondly not only to maintain the activity of the catalyst and selectivity of the hydrogenation reaction but actually to enhance it. This is all the more surprising in that the amount of the additive is in no way sufficient to neutralize the acids present in the hydrogenation and hence to reduce the side reactions.

The alkali metal or alkaline earth metal ions can be added in the form of compounds thereof, although mineral acid salts, even basic mineral acid salts, of the alkali metals and alkaline earth metals are excluded. Preferred alkali metal ions are those which are selected from the group of lithium, sodium, potassium, rubidium and cesium, particular preference being given to lithium, sodium and potassium, very particular preference to sodium and potassium. Preferred alkaline earth metal ions are those selected from the group of magnesium, calcium, strontium and barium, particular preference being given to magnesium and calcium. These alkali metal and/or alkaline earth metal salts are preferably added in the form of the oxides, hydroxides, alkoxides and carboxylates thereof, preferred carboxylates being the carboxylates which are carboxylates of the carboxylic acids of the esters, anhydrides or carboxylic acids to be correspondingly hydrogenated. Particular preference is given to adding the alkali metal and/or alkaline earth metal salts in the form of the hydroxides and carbonates thereof. Very particular preference is given to the addition of alkali metal ions to the hydrogenation feed.

The inventive addition of the alkali metal and/or alkaline earth metal ions is effected in amounts of, based on the amount of the hydrogenation feed, 10 to 2000 ppm, preferably 50 to 1500 ppm, more preferably 100 to 800 ppm, most preferably 200-500 ppm.

The cobalt content of the hydrogenation catalysts, based on the total content by weight in the catalyst, can vary according to catalyst type and is in the range from 0.1 to 99% by weight. The cobalt content of the hydrogenation catalysts in the case of supported catalysts is 0.1 to 20% by weight, preferably 0.5 to 10% by weight, and in the case of unsupported catalysts 10 to 99% by weight, preferably 20 to 99% by weight. When manganese is present, the manganese content in the case of supported catalysts is 0.1 to 10% by weight, preferably 0.2 to 5% by weight, and in the case of unsupported catalysts 0.5 to 30%, preferably 1 to 20% by weight. In addition to the components mentioned, it is also possible for other elements to be present, either in metallic form or as oxides or the like. Metals may also be present in the form of alloys. Examples include Re, Cu, Fe, Mo, Ni and P. In addition, possible elements are those which occur or are added owing to the process for preparing the aforementioned elements from impurities in the catalyst. In general, the content thereof is then below 100 ppm. A preferred catalyst for the process according to the invention has the elements Co, Cu, Mn, Mo, Na and P in the form of oxides thereof in proportions of 60-70% by weight of Co, 15-25% by weight of Cu, 5-10% by weight of Mn, 2-5% by weight of Mo, 0.05-0.5% by weight of Na and 1-3% by weight of P.

The catalysts are activated before the actual hydrogenation. In other words, the oxidic metal components are converted at least partly to the metallic form. This is true of Co in particular. This activation can be effected in the reactor itself, but also elsewhere, in which case the activated catalysts are preferably transported and installed under solvents, for example water or pentanediol, or installed into the reactor having been surface-passivated by means of air. The Co catalysts are preferably activated at temperatures up to 350° C. in a hydrogen stream, to which nitrogen may have been added. Particular preference is given to temperatures up to 300° C.

Alkali metal and/or alkaline earth metal ions can be added in the process according to the invention at particular intervals, but preferably continuously. Continuously is preferred since the addition of alkali metal and/or alkaline earth metal ions, even if they are already present on or in the catalyst as a result of preparation, are washed out by the hydrogenation process. When, in contrast, the alkali metal and/or alkaline earth metal ions are added continuously to the process according to the invention from the start, preferably in amounts of 10 to 2000 ppm, the Co discharge and if appropriate Mn discharge remains at a low level, and the catalyst activity declines less rapidly than without addition. When alkali metal and/or alkaline earth metal ions are added to a catalyst already in operation, it is found that the Co and if appropriate Mn discharges fall, but the activity and selectivity rise.

Moreover, the process according to the invention can increase safety during the hydrogenation. Under some circumstances, Co catalysts exhibit the tendency to uncontrolled exothermic reactions. These can be suppressed by the continuous addition of alkali metal or alkaline earth metal ions.

The hydrogenation conditions which have been established without the inventive addition of alkali metal or alkaline earth metal can also be maintained with the addition of alkali metal or alkaline earth metal. A process for hydrogenating a mixture comprising carboxylic acid, carboxylic anhydride and/or lactones by means of a cobalt-comprising catalyst without using any further alkali metal and/or alkaline earth metal ions can therefore be switched to a process according to the invention without any major problems. The increase in activity on addition of alkali metal and/or alkaline earth metal ions by the process according to the invention can enhance the feed rate and hence also the catalyst hourly space velocity, and also lower the hydrogenation temperature required.

Typical reaction conditions for the process according to the invention are pressures in the range from 100 to 300 bar, preferably in the range from 150 to 290 bar, and reaction temperatures in the range from 150 to 300° C., preferably in the range from 180 to 250° C., and catalyst hourly space velocities in the range from 0.05 to 0.9 kg, more preferably in the range from 0.1 to 0.5 kg, of substance to be hydrogenated/l cat.×hour. Particularly preferred catalyst hourly space velocities are 0.1 to 0.4.

In an industrial scale plant, the procedure is generally to combine the feed together with the outer circulation stream, which serves to supply heat, usually to remove the heat of reaction from the hydrogenation, before they reach the catalyst zone, and optionally to mix them. In doing this, a mixing temperature high enough that the hydrogenation proceeds sufficiently rapidly should be attained. This is generally a temperature between 150 and 295° C., preferably 180 to 220° C. Along the catalyst bed, the temperature then rises as a result of the heat of reaction. In general, this rise is 5 to 70° C., preferably 5 to 30° C. This depends on the ratio of feed to circulation, the heat of reaction and the conversion. The ratio of circulation to feed is generally 1:1 to 30:1, preferably 5:1 to 15:1. The reaction can be divided between several reactors which can be operated in parallel or in series, in trickle mode and/or liquid phase mode. It is advantageous to undertake the majority of the hydrogenation reaction, over 50%, preferably over 80% and more preferably over 90%, in one or more reactors operated with circulation. The rest of the hydrogenation reaction, but without product recycling, should advantageously be performed in straight pass in liquid phase mode or trickle mode.

It has been found to be a preferred variant when the acid number before commencement of the hydrogenation, i.e. directly upstream of the catalyst bed, is between 10 and 90, preferably between 15 and 70, more preferably between 20 and 60. This acid number is established by the ratio of feed to circulation over the reactor or the reactors. When, for example, a circulation rate of 50 to/h is employed with an acid number of 5, and a feed rate of 10 to/h with an acid number of 300, the acid number before reaching the catalyst is approx. 51.

The acid number is defined as the mass of potassium hydroxide in mg which is required to neutralize 1 g of a sample (DIN 53402).

When the acid number is in the range above 90, in spite of metered addition of alkali, there is a relatively rapid decline in the hydrogenation activity of the catalyst. When the acid number is below 10, the metered addition of alkali under some circumstances causes undesired deposition either on the catalyst or in the workup of the hexanediol.

It is also possible to undertake the majority of the reaction not with fixed bed catalyst but in suspension mode.

The hydrogen needed for the hydrogenation is advantageously supplied in a superstoichiometric amount, using, for example, at least two hydrogens per acid function. Advantageously, the excess is 1 to 100% hydrogen, preferably 2 to 20%. The excess hydrogen is typically, optionally together with other gaseous products, for example methane, discharged from the reaction system as offgas, but it is also possible to work without offgas, in which case the discharge employed is the gas dissolved under the reaction conditions, which is discharged in the form of suspended gas after decompression and optional cooling.

Although attempts are generally made to keep the excess of freshly supplied hydrogen as small as possible, it is preferred within the reaction system to have a significant excess of hydrogen present. This can be achieved, for example, by means of cycle gas, in which the gaseous reactor discharge is recycled fully or partly through a cycle gas compressor. The reaction, or at least the main reaction, should preferably be performed in trickle mode, such that a maximum amount of hydrogen is present in a virtually steady state in the system, in order that spent hydrogen can be replenished very rapidly. When cycle gas is employed, this cycle gas stream can be operated in an integrated system with other reactions in which hydrogen is likewise required, for example the hydrogenation of 1,4-butynediol to 1,4-butanediol. This should use an equal pressure level.

The offgas from the hydrogenation, and optionally also the suspended gas, can be made available to other users of hydrogen, but can also be incinerated, optionally to generate power.

The reaction discharges of the hydrogenation are generally worked up by multistage distillation or rectification. This means that several columns are used, in which low boilers such as water and low-boiling alcohols are removed from the product. Low boilers and low-boiling alcohols are understood to mean products which have a boiling point below 100° C. at a pressure of 100 to 500 mbar. Then the product is purified by distillation.

The process according to the invention is illustrated in detail in the examples which follow. The figures for the metal contents were determined by atomic absorption. The acid and ester numbers are determined by titrimetry (mg KOH/g of substance). The percentages reported in the examples below are each based, unless stated otherwise, on weight.

EXAMPLE 1

150 g/h of a mixture of adipic acid (17%), 6-hydroxycaproic acid (16%), glutaric acid (2%), 1.5% 5-hydroxypentanoic acid, 1% formic acid, 1% 1,4-cyclohexanediols, 1% 1,2-cyclohexanediols, 0.3% cyclohexanol/cyclohexanone and other compounds in minor amounts, as can be obtained, for example, by oxygen oxidation of cyclohexane to cyclohexanol/cyclohexanone mixtures and subsequent water scrubbing (approx. 45% water), are hydrogenated at 230° C./250 bar in a 300 ml tubular reactor containing 200 ml of catalyst (66% CoO, 20% CuO, 7.3% $Mn_3O_4$, 3.6% $MoO_3$, 0.1% $Na_2O$, 3% $H_3PO_4$, preparation according to DE-A 23 21 101; 4 mm extrudates; activation with hydrogen up to 300° C.) in trickle mode. The reactor discharge is removed in a separator from excess hydrogen (offgas rate 100 l/h) and passes either via a pump as a circulation stream back to the top of the reactor, where it is combined with the feed stream (feed: circulation=1:10), or into a discharge vessel. The acid number upstream of the catalyst was in the range of 70-75. The discharges were analyzed daily by gas chromatography (% by weight, method with internal standard). After 30 days of test time, the following values were found in the discharge: 1,6-hexanediol: 15.7%, 6-hydroxycaproic acid: 7.4%, 1,5-pentanediol: 3.3%, hexanol: 1.8%, cyclohexyl 1,6-hexanediol ether: 0.1%. The cobalt and manganese contents in the discharge were each approx. 20 ppm. Sodium had fallen below 3 ppm (detection limit) after only 5 test days. The distillative purification of the discharge gave a 1,6-hexanediol purity of 97.5% in addition to 2% 1,4-cyclohexanediols, 0.2% 1,5-pentanediol, 0.1% 1,2-cyclohexanediols, 0.08% cyclohexyl 1,6-hexanediol ether, and further compounds below 500 ppm.

Thereafter, NaOH was added to the feed, such that the NaOH content was 1000 ppm. The resulting mixture was hydrogenated (acid numbers upstream of the catalyst between 60 and 65). In the subsequent days, the yields of the products of value (for example 1,6-hexanediol) rose, while the formation of the hexanol by-product was reduced. After 35 days of test time, i.e. after 5 days of NaOH feeding, the following analysis of the discharge was obtained: 1,6-hexanediol: 18.5%, 6-hydroxycaproic acid: 6.7%, 1,5-pentanediol: 4%, hexanol: 1.4%. The cyclohexyl 1,6-hexanediol ether was not detectable reliably in the crude mixture owing to very small amounts. The cobalt and manganese contents in the discharge were 5 and 11 ppm respectively. The distillative workup gave a similar profile to that without NaOH metering, except that the content of cyclohexyl 1,6-hexanediol ether was below 100 ppm.

EXAMPLE 2

In a 2.5 l tubular reactor, the carboxylic acid solution described in Example 1 was hydrogenated over 2.4 l of the same catalyst as therein. However, the Na content of the discharge was adjusted to 400-500 ppm from the start by adding NaOH to the feed solution. The reactor inlet temperature was 230° C.; the offgas flow rate was 250 l/h. After 5 days of test time, at a feed rate of 1133 g/h, the following product composition was obtained: 28% hexanediol, 1.4% 6-hydroxycaproic acid and 1.4% hexanol. The Co discharge was below 1 ppm, Mn 85 ppm.

In the subsequent days, a feed rate of 1400 g/h was established (acid numbers upstream of the catalyst approx. 55). The hexanediol contents in the discharge were between 27 and 28%. The hydroxycaproic acid content was approx. 2%, hexanol 1.3%. On the 17th test day, 27% hexanediol, 2.3% hydroxycaproic acid and 1.3% hexanol, below 1 ppm of Co, 37 ppm of Mn and 430 ppm of Na were found in the discharge. Thereafter, the sodium feed was stopped. Only 24 h later (18th test day), the Na content in the discharge fell to 7 ppm, but the Co discharge rose to 1 ppm, Mn to 75 ppm. At the same time, the hexanediol content fell to 26%, the hydroxycaproic acid remained at 2.3%, and hexanol rose to 1.4%. These conditions were maintained until the 24th test day. Then the Na content fell to 4 ppm, the Co discharge rose to 2 ppm, and Mn fell to 50 ppm. The hexanediol content fell continuously to 24.8%, and the hydroxycaproic acid rose to 3%, and hexanol to 1.5.

On the 25th test day, Na ions were again metered in, but this time not in the form of NaOH in accordance with the invention, but as $Na_3PO_4$.

After only 24 h, the hexanediol content had fallen to 23.4%, and the hydroxycaproic acid was at 3.6% and hexanol at 1.6%. The Co discharge was 2 ppm, Mn 4 ppm, Na 480 ppm. After a further 28 h, the hexanediol content had already fallen to 18.8%. Hydroxycaproic acid 5%, hexanol 2.2%. In addition, the reactor discharge was biphasic. The test was then terminated.

It was thus found that the sodium salt of the mineral acid $H_3PO_4$ has no inventive ability.

EXAMPLE 3

Example 2 (start settings) was repeated with the difference that the feed to circulation ratio was 1 to 6 and the acid number upstream of the catalyst was approx. 95 after 5 days of test time. The acid number subsequently rose constantly, and approx. 5 ppm of Co and approx. 100 ppm of Mn were found in the discharge after 30 test days. A short time thereafter, the test was terminated since the discharge was again biphasic and the hexanediol content in the discharge was only 15%.

The invention claimed is:
1. A process for preparing diols by hydrogenating a mixture comprising carboxylic acid, carboxylic anhydrides and/or lactones in the presence of a cobalt-comprising catalyst, wherein alkali metal and/or alkaline earth metal ions are added to the hydrogenation feed, excluding alkali metal and/or alkaline earth metal ions of mineral acid salts, and wherein the acid number in the feed upstream of the catalyst which is established by the ratio of feed to circulation over the reactor or the reactors is between 10 and 90.

2. The process according to claim 1, wherein the mixture comprising carboxylic acid, carboxylic anhydride and/or lactones comprises adipic acid, and the hydrogenation is used to prepare 1,6-hexanediol.

3. The process according to claims 1, wherein the amounts of alkali metal and/or alkaline earth metal ions which are added to the hydrogenation feed are in the range from 10 to 2000 ppm, based on the hydrogenation feed.

4. The process according to claim 1, wherein the added alkali metal and/or alkaline earth metal ions are selected from the group consisting of lithium, sodium, potassium, rubidium, cesium, magnesium, calcium, strontium and barium.

5. The process according to claim 1, wherein the added alkali metal and/or alkaline earth metal ions are selected to the hydrogenation feed in the form of the oxides, hydroxides and carboxylates thereof.

6. The process according to claim 1, wherein the cobalt-comprising catalyst comprises a cobalt content in the range from 0.1 to 99% by weight, based on the total weight of the catalyst.

7. The process according to claim 1, wherein the cobalt-comprising catalyst additionally comprises manganese.

8. The process according to claim 1, wherein the hydrogenation is performed at pressures in the range from 100 to 300 bar and temperatures in the range from 150 to 300° C.

9. The process according to claim 1, wherein more than 50% of the hydrogenation reaction is undertaken in one or more reactors which is/are operated with circulation, and the rest of the hydrogenation reaction in straight pass in liquid phase mode or trickle mode.

* * * * *